United States Patent [19]

Ellames et al.

[11] Patent Number: 4,761,414
[45] Date of Patent: Aug. 2, 1988

[54] SUBSTITUTED 1H-PYRIMIDO[1,2-a-]-PYRIDO[3,4-e]PYRAZINE 6 OXIDES

[75] Inventors: George J. Ellames; Roger M. Upton, both of High Wycomb; Albert A. Jaxa-Chamiec, Marlow; Peter L. Myers, Aylesbury, all of United Kingdom

[73] Assignee: G. D. Searle & Co., Chicago, Ill.

[21] Appl. No.: 897,908

[22] Filed: Aug. 19, 1986

[51] Int. Cl.[4] .................. C07D 471/14; C07D 471/20; C07D 239/70; A61K 31/505
[52] U.S. Cl. .................................... 514/250; 544/231; 544/346; 544/242; 544/335
[58] Field of Search ................. 544/231, 346; 514/250

[56] References Cited
PUBLICATIONS

Parthasarathy, Chem. Abs. 101, 55037b.
Parthasarathy et al., Ind. J. Chem. 22B, 1233, 1250 (1983).
Strauss, J. Org. Chem. 43, 2041 (1978).

*Primary Examiner*—Mark L. Berch
*Attorney, Agent, or Firm*—Mary Jo Kanady; Paul D. Matukaitis; R. E. L. Henderson

[57] ABSTRACT

This disclosure relates to a compound of the formula:

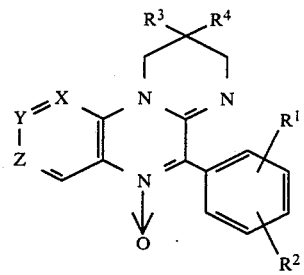

or a pharmaceutically acceptable salt thereof, wherein $R^1$ and $R^2$ are independently selected from the class consisting of hydrogen, halo, $C_1$-$C_6$ alkyl, and $C_1$-$C_6$ alkoxy;

$R^3$ and $R^4$ are independently hydrogen or $C_1$-$C_6$ alkyl or $R^3$ and $R^4$ together may be a

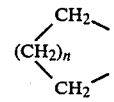

group wherein n is an integer of from 0 to 4; and
X, Y and Z are independently —CH— or —N= provided that one and only one of X, Y or Z must be —N=.

The disclosure further relates to pharmaceutical compositions containing such compounds and to the use of such compounds and compositions as anti-anaerobic agents.

53 Claims, No Drawings

SUBSTITUTED 1H-PYRIMIDO[1,2-a]-PYRIDO[3,4-e]PYRAZINE 6-OXIDES

This invention relates to a novel class of substituted 1H-pyrimido[1,2-a]-pyrido[3,4-e]pyrazine 6-oxides. The present invention further relates to pharmacetical compositions containing such compounds and to the use of such compounds and compositions as anti-anaerobic agents.

BACKGROUND OF THE INVENTION

Parthasarathy, et al., *Indian Journal of Chemistry*, 22B, 1250–1251 (1983), describe a class of substituted 1,2-dihydroimidazo[1,2-a]quinoxaline 5-oxides that have antiamoebic activity against *Entamoeba histolytica* in intestinal and hepatic amoebiasis. Parthasarathy, et al., *Indian Journal of Chemistry*, 22B, p. 1233–1235 (1983), describe certain N-oxides of 2,3-dihydro-1H-pyrimido[2,1-h]pteridines; 1,2-dihydroimidazo[2,1-h]pteridines; 10-aza-2,3-dihydro-1H-pyrimido[1,2-a]quinoxalines; 9-aza-1,2-dihydroimidazo[1,2-a]quinoxalines and 7-aza-1,2-dihydroimidazo[1,2-a]quinoxalines which possess antiamoebic activity in particular against hepatic amoebiasis. Strauss, et al., *J. Org. Chem.*, 43, 2041–2044 (1978), describe the preparation of quinoxaline and dihydroimidazoquinoxaline N-oxides.

SUMMARY OF THE INVENTION

The present invention relates to a class of novel compounds of the formula

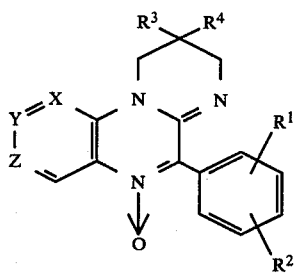

wherein
$R^1$ and $R^2$ are independently selected from the class consisting of hydrogen, halo, $C_1$–$C_6$ alkyl, and $C_1$–$C_6$ alkoxy;
$R^3$ and $R^4$ are independently hydrogen or $C_1$–$C_6$ alkyl or $R^3$ and $R^4$ together may be a

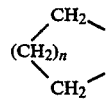

group wherein n is an integer of from 0 to 4; and X, Y, and Z are independently —CH— or —N═ provided that one and only one of X, Y, or Z must be —N═;
and pharmaceutically acceptable salts thereof.

The present invention further relates to pharmaceutical compositions containing such compounds and to the use of such compounds as anti-anaerobic agents.

The term "$C_1$–$C_6$ alkyl" specified herein includes straight chain or branched chain hydrocarbon groups having from one to six carbon atoms respectively. Illustrative of such alkyl groups are methyl, ethyl, propyl, isopropyl, butyl, isobutyl, sec-butyl, tert-butyl, pentyl, neopentyl, hexyl, isohexyl, and the like.

The term "$C_1$–$C_6$ alkoxy" specified herein includes straight chain or branched chain alkoxy groups having from one to six carbon atoms respectively. Representative of such alkoxy groups are, for example, methoxy, ethoxy, propoxy, isopropoxy, butoxy, t-butoxy, pentoxy, hexoxy and the like.

As used herein the term "halogen or halo" refers to fluoro, chloro, iodo and bromo.

DETAILED DESCRIPTION OF THE INVENTION

The compounds of the present invention may be prepared in accordance with the following general procedure:

A substituted tetrahydropyrimidine of the formula

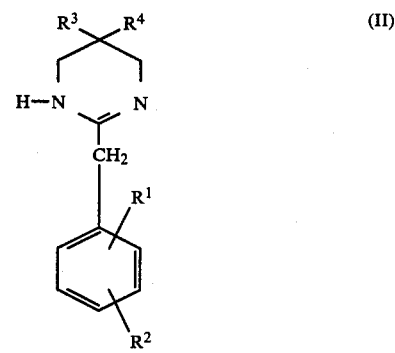

wherein $R^1$, $R^2$, $R^3$ and $R^4$ are as above defined; is reacted with a substituted nitroaromatic of the formula

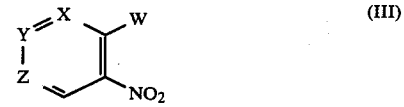

wherein W is halo; and X, Y and Z are as above defined; under basic conditions in an appropriate solvent such as isopropyl alcohol or acetonitrile, to yield the compounds of the formula:

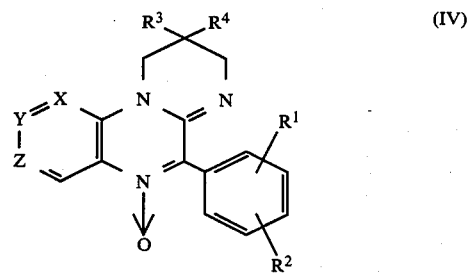

The pharmaceutically acceptable salts of the compounds of formula (IV) may be prepared by conventional procedures, such as by reacting the free base in a suitable solvent, e.g. diethylether or ethanol, with a solution containing one equivalent of the desired acid in a suitable solvent, e.g. diethylether or ethanol. The salt generally precipitates from solution or is recovered by evaporation of the solvent. Such pharmaceutically acceptable salts include, for example, hydrochloride, sulfate, phosphate, and the like.

A preferred embodiment includes compounds of the formula

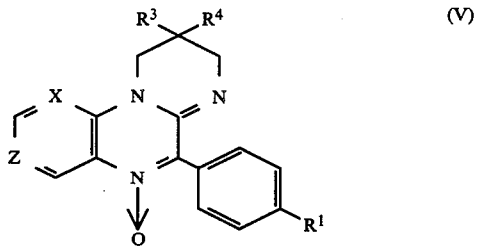

wherein X, Z, $R^1$, $R^3$ and $R^4$ are as above defined.

A more preferred embodiment encompasses compounds of formula (V) wherein $R^1$ is hydrogen and $R^3$ and $R^4$ are independently $C_1$-$C_6$ alkyl.

The appropriate solvents employed in the above reactions are solvents in which the reactants are soluble but which do not react with the reactants. The preferred solvents vary from reaction to reaction and are readily ascertained by one of ordinary skill in the art.

The compounds of the present invention may be administered by any suitable route, preferably in the form of a pharmaceutical composition adapted to such a route and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and, if desired, other active ingredients. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient of about 1 to 250 mg, preferably about 25 to 150 mg. A suitable daily dose for a mammal may vary widely depending on the condition of the patient and other factors. However, a dose of about 0.1 to 300 mg/kg body weight, particularly of about 1 to 100 mg/kg body weight may be appropriate.

The active ingredient may also be administered by injection as a composition wherein, for example, saline, dextrose or water may be used as a suitable carrier. A suitable daily dose is about 0.1 to 100 mg/kg body weight injected per day in multiple doses depending on the disease being treated. A preferred daily dose would be about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration and well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include, for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

As previously mentioned, the compounds and compositions of the present invention are effective as antianaerobic agents for the treatment of infectious diseases related to anaerobic bacteria. Representative of infectious diseases that may be treated with the compounds and compositions of the present invention include, for example, post operative sepsis following lower gastrointestinal surgery or female urinogenital surgery, pelvic inflammatory disease, ulcers, gangrene, trichomonal vaginitis, non-specific vaginitis, amoebiasis, giardiasis, periodontal disease, acne and the like.

The following Examples are intended to further illustrate the present invention and not to limit the invention in spirit or scope. In the Examples, all parts are parts by weight unless otherwise expressly set forth.

EXAMPLE 1

1,4,5,6-Tetrahydro-5-ethyl-5-methyl-2-(phenylmethyl)-pyrimidine

Tolazoline (9.6 g, 60 mmol) and 2-ethyl-2-methylpropane-1,3-diamine (7.3 g, 63 mmol) were stirred together at 100° C. until homogeneous. Toluene (600 ml) was added to the reaction mixture and the resulting mixture was azeotropically distilled to remove ethylenediamine. This process was repeated following addition of additional toluene (800 ml) to yield an oil. This oil was chromatographed on silica gel in methanol:saturated aqueous ammonia:ethyl acetate (1:1:18) to yield a pale yellow oil, which upon standing yielded a waxy solid, 1,4,5,6-tetrahydro-5-ethyl-5-methyl-2-(phenylmethyl)-pyrimidine (5.5 g), ($\delta$(CDCl$_3$) 0.80 (2×3H, t+s), 1.22

(2H, q), 2.90 (3H, m), 3.56 (3H, m) and 7.10–7.40 (5H, m)) represented by the structural formula:

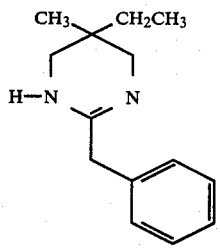

EXAMPLES 2-8

The following compounds were prepared in accordance with the reaction conditions employed in Example 1 using appropriate starting materials;

EXAMPLE 2

1,4,5,6-Tetrahydro-5,5-dimethyl-2-(phenylmethyl)-pyrimidine off white, waxy solid, ($\delta$(CDCl$_3$) 0.9 (6H, s), 2.90 (4H, s), 3.49 (2H, s), 5.1–5.2 (1H, br) and 7.12–7.33 (5H, m)) represented by the structural formula:

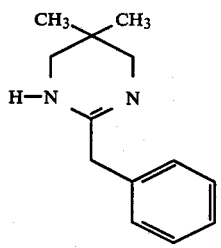

EXAMPLE 3

1,4,5,6-Tetrahydro-2-[(4-chlorophenyl)methyl]-5,5-dimethylpyrimidine: crystalline solid, m.p. 130°–132° C., from ethyl acetate (Found: C, 65.48, H, 7.18, N, 11.84%; C$_{12}$H$_{17}$ClN$_2$ requires C, 65.46, H, 7.27, N, 11.74%) represented by the structural formula:

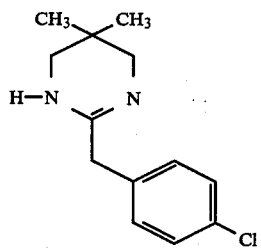

EXAMPLE 4

1,4,5,6-Tetrahydro-5,5-dimethyl-2[(3,4-dimethoxyphenyl)methyl]pyrimidine: off-white solid, ($\delta$(CDCl$_3$)) 0.91 (6H, s), 2.94 (4H, s, 3.47 (6H, s), 4.2–4.4 (1H, br), and 6.76–6.90 (3H, m)), represented by the structural formula:

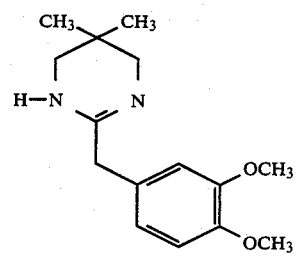

EXAMPLE 5

1,4,5,6-Tetrahydro-5,5-dimethyl-2[(4-methylphenyl)-methyl]pyrimidine: off-white waxy solid, ($\delta$(CDCl$_3$) 0.9 (6H, s), 2.33 (3H, s), 2.91 (4H, s), 3.47 (2H, s), 4.18–4.41 (1H, br) and 7.10–7.24 (4Hm)), represented by the structural formula:

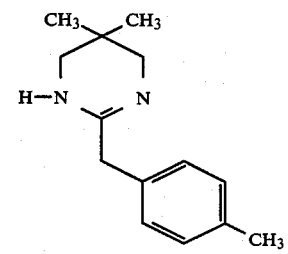

EXAMPLE 6

1,4,5,6-Tetrahydro-5,5-diethyl-2-(phenylmethyl)-pyrimidine: white waxy solid; ($\delta$(CDCl$_3$) 0.80 (6H, t, J=8 Hz), 1.25 (4H, q, J=8 Hz), 2.98 (3H, s) 3.50–3.64 (3H, m), 7.11–7.40 (5H, m)), represented by the structural formula:

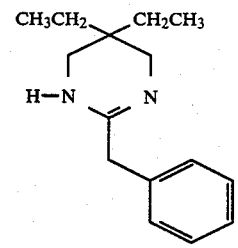

EXAMPLE 7

1,4,5,6-Tetrahydro-5-methyl-2-(phenylmethyl)-5-propylpyrimidine: white waxy solid, ($\delta$(CDCl$_3$) 0.84 (3H, s), 0.86 (3H, t, J=7 Hz), 1.08–1.39 (4H, m), 2.85–3.02 (3H, m), 3.50–3.62 (3H, m) and 7.13–7.40 (5H, m)), represented by the structural formula:

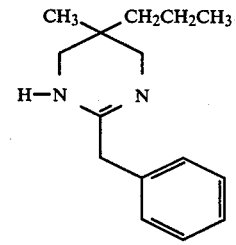

EXAMPLE 8

8,10-Diaza-9-(phenylmethyl)spiro[5.5]undec-9-ene: pale yellow oil, ($\delta$(CDCl$_3$)1.27 (3H, br), 1.44 (7H, br), 3.00 (3H, s), 3.48–3.64 (3H, m) and 7.24–7.33 (5H, m), represented by the structural formula:

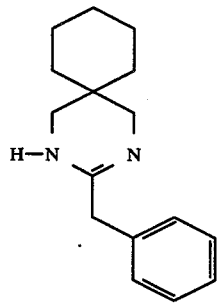

EXAMPLE 9

1,4,5,6-Tetrahydro-5,5-dimethyl-2-[(4-fluorophenyl)methyl]pyrimidine: white, waxy solid, ($\delta$(CDCl$_3$) 0.92 (6H, s), 2.94 (4H, s), 3.44 (2H, s), 6.96–7.06 and 7.22–7.33 (4H, m)) represented by the structural formula:

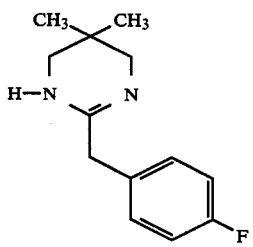

EXAMPLE 10

1,4,5,6-Tetrahydro-5-methyl-2-(phenylmethyl)pyrimidine: yellow waxy solid, ($\delta$(CDCl$_3$) 0.94 (3H, d), 1.79–1.90 (1H, m) 2.77–2.90 (2H, m), 3.26–3.36 (2H, m), 3.60 (2H, s), 5.83–6.10 (1H, b), 7.26–7.38 (5H, m)) represented by the structural formula:

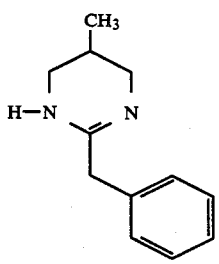

EXAMPLE 11

1,4,5,6-Tetrahydro-5-ethyl-5-methyl-2-[(4-methylphenyl)methyl]pyrimidine: waxy solid ($\delta$(CDCl$_3$) 0.84 (2×3H, t+s), 1.26 (2H, q), 2.33 (3H, s), 2.94 (4H, m), 3.51 (2H, bs), and 7.09–7.22 (4H, q) represented by the structural formula:

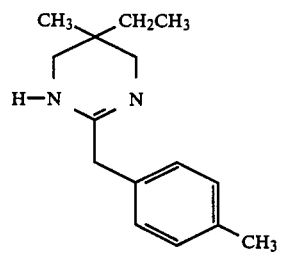

EXAMPLE 12

1,4,5,6-Tetrahydro-5,5-dipropyl-2-(phenylmethyl)pyrimidine: colorless solid, m.p. 98°–99° C., (Found: C, 78.85, H, 10.07, N, 10,88%; C$_{17}$H$_{26}$N$_2$ requires C, 79.02, H, 10.14, N, 10.84%) represented by the structural formula:

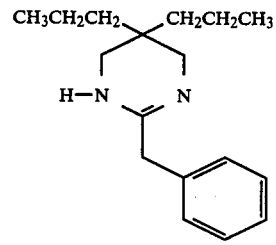

EXAMPLE 13

4-Fluoro-3-nitropyridine

Anhydrous potassium fluoride (5.5 g, 93 mmol) was suspended in anhydrous dimethylsulfoxide (200 ml) and the solvent reduced to half its volume by distillation under an atmosphere of nitrogen. The resulting suspension was cooled to room temperature and 4-chloro-3-nitropyridine (14 g, 88 mmol) was added. The reaction mixture was stirred at 120° C. for three hours under an atmosphere of nitrogen, cooled and then poured into a saturated aqueous solution of potassium dihydrogen phosphate. The resulting mixture was extracted with ethyl acetate. The organic phase was washed three times with water and then brine before being dried over anhydrous magnesium sulphate. The solvent was removed in vacuo to yield as an oil, 4-fluoro-3-nitropyridine (6.5 g), ($\delta$(CDCl$_3$) 7.32 (1H, 4 lines), 7.86 (1H, t, J=5 Hz) and 8.29 (1H, d, J=9 Hz), represented by the structural formula:

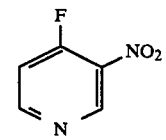

EXAMPLE 14

2,3-Dihydro-2,2-dimethyl-5-phenyl-1H-pyrimido[1,2-a]pyrido[4,3-e]pyrazine 6-oxide 3-Fluoro-4-nitropyridine (0.5 g, 3.5 mmol), potassium carbonate (0.3 g, 2.2 mmol) and 1,4,5,6-tetrahydro-5,5-dimethyl-2-(phenylmethyl)pyrimidine (0.7 g, 3.45 mmol) were heated together in acetonitrile at 40° C. for 1 hr under an atmosphere of nitrogen. The solvent was then removed in vacuo and the organic residue dissolved in dichloromethane and dried over anhydrous magnesium sulphate. The solvent was removed in vacuo and the crude product chromatographed on silica gel in methanol:dichloromethane (1:19) to yield a yellow solid that was recrystallized from ethyl acetate to yield 2,3-dihydro-2,2-dimethyl-5-phenyl-1H-pyrimido[1,2-a]pyrido[4,3-e]pyrazine 6-oxide (0.31 g), m.p. 231°–233° C., (Found: C, 70.51, H, 5.82, N, 18.14%; $C_{18}H_{18}N_4O$ requires C, 70.57, H, 5.92, N, 18.29%) represented by the structural formula:

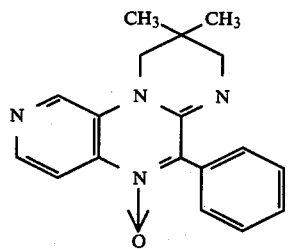

EXAMPLE 15-32

The following compounds were prepared in accordance with the reaction conditions employed in Example 14 using appropriate starting materials.

EXAMPLE 15

2,3-Dihydro-2,2-dimethyl-5-phenyl-1H-pyrimido[1,2-a]pyrido[3,4-e]pyrazine 6-oxide: yellow crystalline solid, m.p. 249°–251° C., (Found: C, 69.84, H, 5.81, N, 17.92%; $C_{18}H_{18}N_4O \cdot 0.2H_2O$ requires C, 69.75, H, 5.98, N, 18,07%) represented by the structural formula:

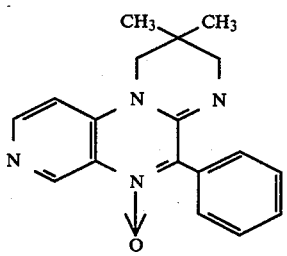

EXAMPLE 16

2,3-Dihydro-2,2-dimethyl-5-phenyl-1H-pyrimido[1,2-a]pyrido[3,2-e]pyrazine 6-oxide: yellow crystalline solid, m.p. 212°–214° C., (Found: C, 70.4, H, 5.9, N, 18.2%; $C_{18}H_{18}N_4O$ requires C, 70.6, H, 5.9, N, 18.3%) represented by the structural formula:

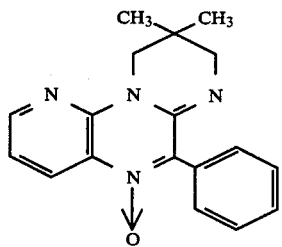

EXAMPLE 17

2,3-Dihydro-5-(4-chlorophenyl)-2,2-dimethyl-1H-pyrimido[1,2-a]pyrido[3,4-e]pyrazine 6-oxide: bronze crystalline solid, m.p. 233°–234° C., (Found: C, 63.33, H, 4.96, N, 16.38%; $C_{18}H_{17}ClN_4O$ requires C, 63.44 H, 5.03, N, 16.44%) represented by the structural formula:

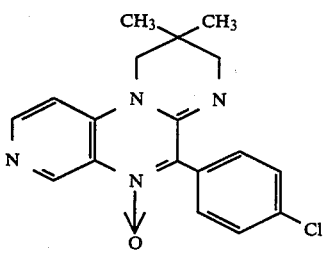

EXAMPLE 18

2,3-Dihydro-5-(4-chlorophenyl)-2,2-dimethyl-1H-pyrimido[1,2-a]pyrido[3,2-e]pyrazine 6-oxide: yellow crystalline solid, m.p. 118°–119° C., (Found: C, 63.83, H, 5.00, N, 16.45%; $C_{18}H_{17}ClN_4O$ requires C, 63.44, H, 5.03, N, 16.44%) represented by the structural formula:

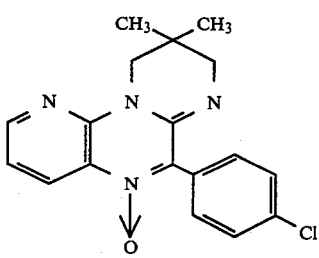

EXAMPLE 19

2,3-Dihydro-2,2-dimethyl-5-(4-methylphenyl)-1H-pyrimido[1,2-a]pyrido[3,4-e]pyrazine 6-oxide: yellow crystalline solid, m.p. 179°–181° C., (Found: C, 71.59, H, 6.29, N, 17.36%; $C_{19}H_{20}N_4O$ requires C, 71.23, H, 6.29, N, 17.49%) represented by the structural formula:

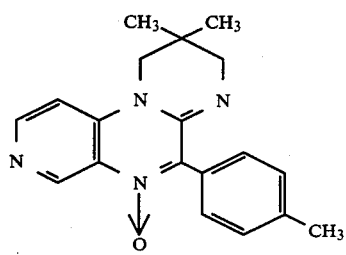

EXAMPLE 20

2,3-Dihydro-2,2-dimethyl-5-(4-methylphenyl)-1H-pyrimido[1,2-a]pyrido[3,2-e]pyrazine 6-oxide: yellow crystalline solid, m.p. 220°–225° C., (Found: C, 70.27, H, 6.28, N, 17.22%; $C_{19}H_{20}N_4O \cdot 0.2H_2O$ requires C, 70.44, H, 6.28, N, 17.22%) represented by the structural formula:

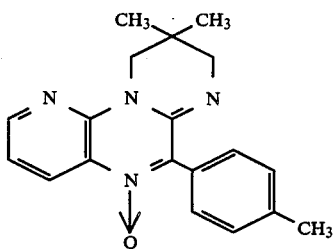

EXAMPLE 21

2,3-Dihydro-5-(3,4-dimethoxyphenyl)-2,2-dimethyl-1H-pyrimido[1,2-a]pyrido]3,4-e]pyrazine 6-oxide: yellow crystalline solid, m.p. 200°–202° C., (Found: C, 65.33, H, 5.98, N, 14.91%; $C_{20}H_{22}N_4O_3.0.1H_2O$ requires C, 65.24, H, 6.08, N, 15.22%) represented by the structural formula:

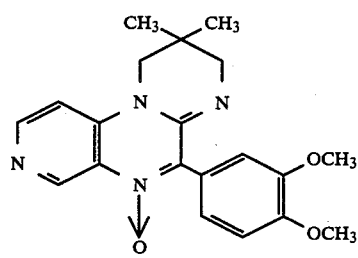

EXAMPLE 22

2,3-Dihydro-5-(3,4-dimethoxyphenyl)-2,2-dimethyl-1H-pyrimido[1,2-a]pyrido[3,2-e]pyrazine 6-oxide: yellow crystalline solid, m.p. 127°–129° C., (Found: C, 65.34, H, 5.98, N, 15.14%; $C_{20}H_{22}N_4O_3$ requires C, 65.56, H, 6.05, N, 15.29%) represented by the structural formula:

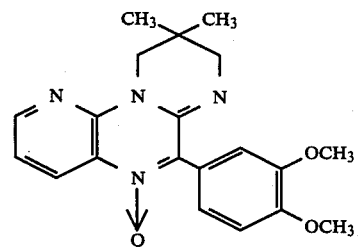

EXAMPLE 23

2,3-Dihydro-2-ethyl-2-methyl-5-phenyl-1H-pyrimido[1,2-a]pyrido[3,4-e]pyrazine 6-oxide: yellow crystalline solid m.p. 189°–190° C., (Found: C, 71.18, H, 6.28, N, 17.43%; $C_{19}H_{20}N_4O$ requires C, 71.23, H, 6.29, N, 17.49%) represented by the structural formula:

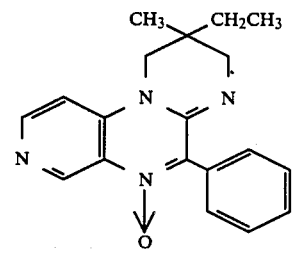

EXAMPLE 24

2,3-Dihydro-2-ethyl-2-methyl-5-phenyl-1H-pyrimido[1,2-a]pyrido[3,2-e]pyrazine 6-oxide: orange crystalline solid, m.p. 157°–159° C., (Found: C, 71.25, H, 6.36, N, 17.49%; $C_{19}H_{20}N_4O$ requires C, 71.23, H, 6.29, N, 17.49%) represented by the structural formula:

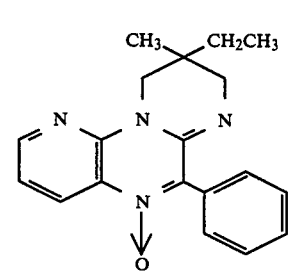

EXAMPLE 25

2,3-Dihydro-2,2-diethyl-5-phenyl-1H-pyrimido[1,2-a]pyrido[3,4-e]pyrazine 6-oxide: light brown crystalline solid, m.p. 139°–141° C., (Found: C, 71.15, H, 6.57, N, 16.57%; $C_{20}H_{22}N_4O.0.2H_2O$ requires C, 71.07, H, 6.68, N, 16.57%) represented by the structural formula:

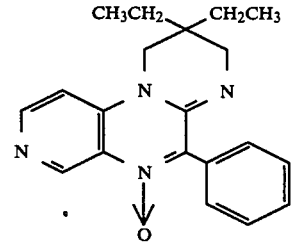

EXAMPLE 26

2,3-Dihydro-2,2-diethyl-5-phenyl-1H-pyrimido[1,2-a]pyrido[3,2-e]pyrazine 6-oxide: light brown crystalline solid, m.p. 120°–121° C., (Found: C, 71.05, H, 6.51, N, 16.71%; $C_{20}H_{22}N_4O.0.2H_2O$ requires C, 71.07, H, 6.68, N, 16.57%) represented by the structural formula:

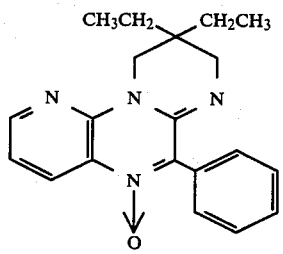

EXAMPLE 27

2,3-Dihydro-2-methyl-5-phenyl-2-propyl-1H-pyrimido[1,2-a]pyrido[3,4-e]pyrazine 6-oxide: yellow crystalline solid, m.p. 163°–166° C., (Found: C, 71.79, H, 6.68, N, 16.77%; $C_{20}H_{22}N_4O$ requires C, 71.83, H, 6.63, N, 16.75%) represented by the structural formula:

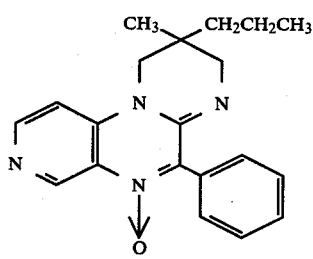

EXAMPLE 28

2,3-Dihydro-2-methyl-5-phenyl-2-propyl-1H-pyrimido[1,2-a]pyrido[3,2-e]pyrazine 6-oxide: yellow crystalline solid, m.p. 129°–130° C., (Found: C, 71.53, H, 6.67, N, 16.68%; $C_{20}H_{22}N_4O$ requires C, 71.83, H, 6.63, N, 16.75%) represented by the structural formula:

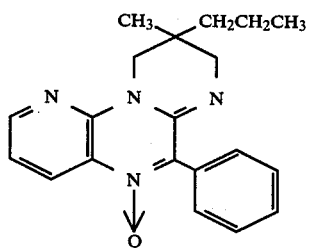

EXAMPLE 29

Spiro[cyclohexane-1,2'-[2,3]-dihydro-[5]-phenyl-[1H]pyrimido[1,2-a]pyrido[3,2-e]pyrazine [6]-oxide]: orange crystalline solid, m.p. 182°–185° C., (Found: C, 71.85, H, 6.37, N, 16.29%; $C_{21}H_{22}N_4O.0.2H_2O$ requires C, 72.08, H, 6.41, N, 16.02%) represented by the structural formula:

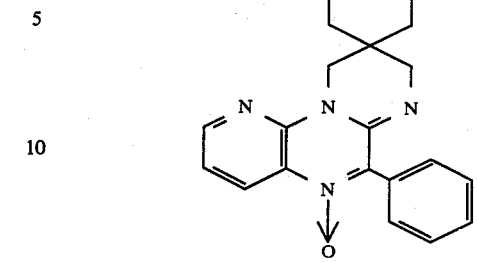

EXAMPLE 30

Spiro[cyclohexane-1,2'-[2,3]-dihydro-[5]-phenyl-[1H]pyrimido[1,2-a]pyrido[3,4-e]pyrazine [6]-oxide]: yellow crystalline solid, m.p. 215°–217° C., (Found: C, 72.66, H, 6.52, N, 16.10%; $C_{21}H_{22}N_4O$ requires C, 72.81, H, 6.40, N, 16.17%) represented by the structural formula:

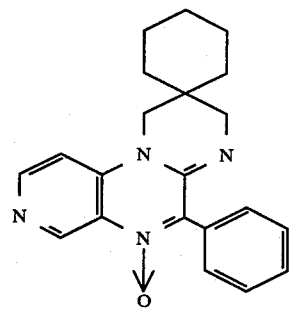

EXAMPLE 31

2,3-Dihydro-2,2-dimethyl-5-(4-fluorophenyl)-1H-pyrimido[1,2-a]pyrido[3,2-e]pyrazine 6-oxide: yellow crystalline solid, m.p. 220°–222° C., (Found: C, 66.57, H, 5.37, N, 17.28%; $C_{18}H_{17}FN_4O$ requires C, 66.65, H, 5.28, N, 17.27%) represented by the structural formula:

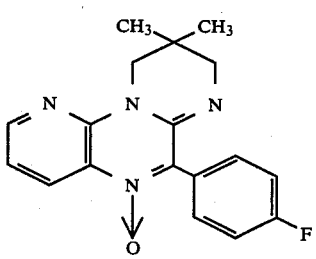

EXAMPLE 32

2,3-Dihydro-2-methyl-5-phenyl-1H-pyrimido[1,2-a]pyrido[3,2-e]pyrazine 6-oxide: golden yellow crystalline solid, m.p. 162°–164° C., (Found: C, 69.73, H, 5.63, N, 19.16%; $C_{17}H_{16}N_4O$ requires C, 69.84, H, 5.52, N, 19.16%) represented by the structural formula:

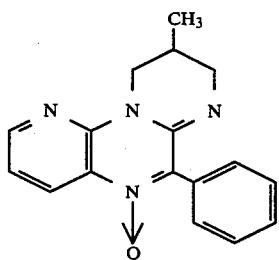

EXAMPLE 33

2,3-Dihydro-2,2-dimethyl-5-(4-fluorophenyl)-1H-pyrimido[1,2-a]pyrido[3,4-e]pyrazine 6-oxide: yellow crystalline solid, m.p. 204°-205° C., (Found: C, 66.50, H, 5.31, N, 17.17%; $C_{18}H_{17}FN_4O$ requires C, 66.65, H, 5.28, N, 17.27%) represented by the structural formula:

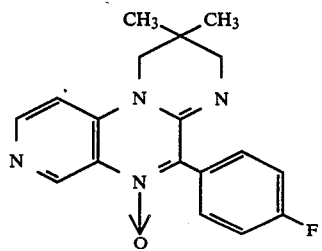

EXAMPLE 34

2,3-Dihydro-2-methyl-5-phenyl-1H-pyrimido[1,2-a]pyrido[3,4-e]pyrazine 6-oxide: yellow crystalline solid, m.p. 145°-147° C., (Found: C, 69.59, H, 5.61, N, 18.94%; $C_{17}H_{16}N_4O$ requires C, 69.84, H, 5.52, N, 19.16%) represented by the structural formula:

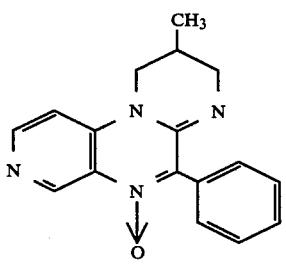

EXAMPLE 35

2,3-Dihydro-2-ethyl-2-methyl-5-(4-methylphenyl)-1H-pyrimido[1,2-a]pyrido[3,2-e]pyrazine 6-oxide: yellow crystalline solid, m.p. 158°-160° C., (Found: C, 71.67, H, 6.67, N, 16.7%; $C_{20}H_{22}N_4O$ requires C, 71.83, H, 6.64, N, 16.75%) represented by the structural formula:

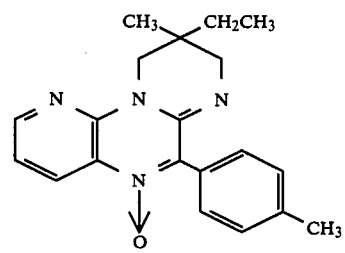

EXAMPLE 36

2,3-Dihydro-2-ethyl-2-methyl-5-(4-methylphenyl)-1H-pyrimido[1,2-a]pyrido[3,4-e]pyrazine 6-oxide: yellow crystalline solid, m.p. 182°-184° C. (Found: C, 71.79, H, 6.64, N, 17.01%; $C_{20}H_{22}N_4O$ requires C, 71.83, H, 6.63, N, 16.75%) represented by the structural formula:

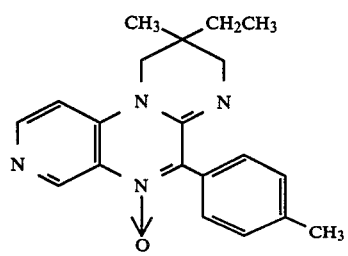

EXAMPLE 37

2,3-Dihydro-2,2-dipropyl-5-phenyl-1H-pyrimido[1,2-a]pyrido[3,2-e]pyrazine 6-oxide: yellow crystalline solid, m.p. 158°-159° C., (Found: C, 72.43, H, 7.26, N, 15.25%; $C_{22}H_{26}N_4O.0.1H_2O$ requires C, 72.54, H, 7.20, N, 15.38%) represented by the structural formula:

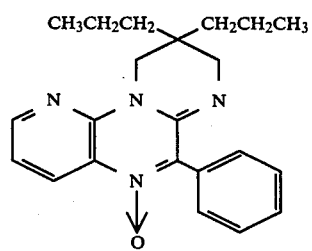

EXAMPLE 38

2,3-Dihydro-2,2-dipropyl-5-phenyl-1H-pyrimido[1,2-a]pyrido[3,4-e]pyrazine 6-oxide: yellow crystalline solid, m.p. 188°-190° C., (Found: C, 72.91, H, 7.26, N, 15.49%; $C_{22}H_{26}N_4O$ requires C, 72.90, H, 7.23, N, 15.46%) represented by the structural formula:

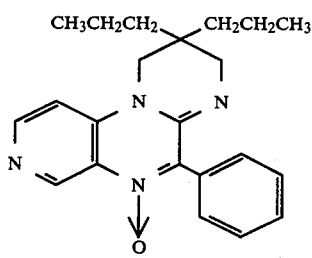

EXAMPLE 39

2,3-Dihydro-2,2-dimethyl-5-phenyl-1H-pyrimido[1,2-a]pyrido[3,2-e]pyrazine 6-oxide bishydrochloride The compound from Example 16 (1.3 g) was suspended in ethyl acetate (40 ml) and dichloromethane added until the reaction was complete. An anhydrous solution of hydrogen chloride in diethyl ether (15 ml, 1M) was added dropwise to the reaction mixture with stirring. The resulting mixture was triturated with dry ether to yield 2,3-dihydro-2,2-dimethyl-5-phenyl-1H-pyrimido[1,2-a]pyrido[3,2-e]pyrazine 6-oxide bishydrochloride (1.54 g), as pale yellow crystals, m.p. 163°–168° C., (Found: C, 57.07, H, 5.33, N, 14.81%; $C_{18}H_{18}N_4O \cdot 2HCl$ requires C, 57.00, H, 5.31, N, 14.77%) represented by the structural formula:

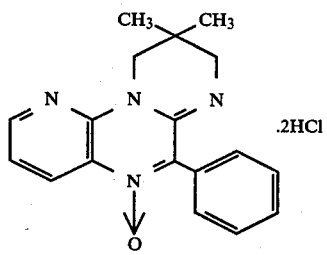

EXAMPLE 40

The screening panel utilized in this Example consisted of 5 strains of *Bacteroides fragilis*. All assays were carried out in 96-well microtitre plates. If an isolate was obtained from either a culture collection or clinical source, the isolate was immediately inoculated into Wilkens-Chalgren broth (Oxoid) and incubated at 37° C. in an anaerobic chamber in an atmosphere of 85% nitrogen, 10% carbon dioxide, and 5% hydrogen for 48 hours. At the end of this time, the viable count was about $10^{12}$ organisms/ml broth. A 1 ml aliquot of each culture was placed in an ampoule and quick frozen in acetone-dry ice mixture and stored in liquid nitrogen. When an inoculum was utilized in an assay, one of the ampoules was thawed and diluted with fresh broth to yield a suspension having a count of $5 \times 10^5$ organisms/ml. A 100 μl aliquot of this suspension was inoculated into each well of the microtitre plate.

A 2 mg sample of the test compound was dissolved in 0.2 ml of a suitable solvent such as dimethylsulfoxide, polyethylene glycol 200 or methanol. The solution was then diluted with 4.8 ml of water to yield a solution having a concentration of 400 mg/L. Doubling dilutions of this stock were prepared to give a range of concentrations from 1.6–200 mg/L. 100 μl of each concentration were then placed in the wells of a microtitre plate containing the inoculum to produce a mixture having a final concentration in the range of 0.8–100 mg/L. Metronidazole was employed as a positive control and solvent/water mixture was employed as a negative control. After addition of the test solution the final inoculum level was $10^5$ cells/ml. The plates were incubated for 48 hours at 37° C. in the anaerobic chamber. The Minimum Inhibitory Concentration (MIC) was read visually. The MIC is defined as the lowest concentration at which there is no detectable growth. The Minimum Bactericidal Concentration (MBC) was determined by taking 50 μl aliquot from each well and placing it in fresh medium. The MBC is defined as the lowest concentration at which there are less than 5 colonies (i.e. 99.9% reduction in viable count) after 48 hours of incubation. The MIC and MBC values for each compound tested and the respective MIC and MBC value for metronidazole are indicated in Table 1. The MIC and MBC value for the negative control that was assayed along with each test compound was greater than 100 mg/L. The MIC and MBC values in table 1 are expressed in mg/L. A blank in the table represented by a "13" indicates that the assay was not conducted using the strain indicated.

The strains of Bacteroides fragilis utilized in the above procedure are identified by letter in accordance with the following legend:

| Strain | Organism |
|---|---|
| A | *B. fragilis* NCTC 10581 |
| B | *B. fragilis* NCTC 9343 |
| C | *B. fragilis* NCTC 9344 |
| D | *B. fragilis* MZ-R ATCC 11295 |
| E | *B. fragilis* WS-1* |

*Obtained from St. Thomas's Hospital Medical School, London, United Kingdom.

TABLE 1

| Compound of Example No. | Strain A MIC | A MBC | B MIC | B MBC | C MIC | C MBC | D MIC | D MBC | E MIC | E MBC |
|---|---|---|---|---|---|---|---|---|---|---|
| 14 | 6.2 | 12.5 | 3.1 | 6.2 | 6.2 | 6.2 | 3.1 | 3.1 | 3.1 | 3.1 |
| Metronidazole | <0.8 | <0.8 | <0.8 | <0.8 | <0.8 | <0.8 | 6.2 | 6.2 | <0.8 | <0.8 |
| 15 | <0.8 | <0.8 | <0.8 | <0.8 | <0.8 | <0.8 | <0.8 | 1.5 | <0.8 | 1.5 |
| Metronidazole | <0.8 | <0.8 | <0.8 | <0.8 | <0.8 | <0.8 | 6.2 | 6.2 | <0.8 | <0.8 |
| 16 | 3.1 | 3.1 | 1.5 | 1.5 | 1.5 | 1.5 | <0.8 | 1.5 | <0.8 | 1.5 |
| Metronidazole | 1.5 | 1.5 | <0.8 | 1.5 | <0.8 | 1.5 | 12.5 | 12.5 | 3.1 | 3.1 |
| 17 | <0.8 | <0.8 | 1.5 | 1.5 | <0.8 | <0.8 | <0.8 | <0.8 | <0.8 | <0.8 |
| Metronidazole | <0.8 | <0.8 | <0.8 | <0.8 | <0.8 | <0.8 | 6.2 | 12.5 | <0.8 | <0.8 |
| 18 | <0.8 | <0.8 | <0.8 | <0.8 | 1.5 | 1.5 | <0.8 | <0.8 | <0.8 | <0.8 |
| Metronidazole | <0.8 | <0.8 | <0.8 | <0.8 | 1.5 | 1.5 | 6.2 | 12.5 | <0.8 | <0.8 |
| 19 | 1.5 | 1.5 | <0.8 | 1.5 | <0.8 | <0.8 | 1.5 | 1.5 | 1.5 | 1.5 |
| Metronidazole | <0.8 | 1.5 | <0.8 | <0.8 | <0.8 | <0.8 | 12.5 | 50 | 1.5 | 3.1 |
| 20 | <0.8 | <0.8 | 6.2 | 6.2 | 1.5 | 1.5 | <0.8 | <0.8 | 1.5 | <0.8 |
| Metronidazole | 1.5 | 1.5 | 3.1 | 3.1 | 3.1 | 3.1 | 6.2 | 6.2 | 1.5 | 3.1 |

TABLE 1-continued

| Compound of Example No. | Strain A MIC | A MBC | B MIC | B MBC | C MIC | C MBC | D MIC | D MBC | E MIC | E MBC |
|---|---|---|---|---|---|---|---|---|---|---|
| 21 | <0.8 | <0.8 | 1.5 | 1.5 | <0.8 | 1.5 | <0.8 | <0.8 | <0.8 | <0.8 |
| Metronidazole | <0.8 | <0.8 | <0.8 | <0.8 | <0.8 | <0.8 | 6.2 | 6.2 | <0.8 | <0.8 |
| 22 | 1.5 | 1.5 | <0.8 | <0.8 | <0.8 | <0.8 | <0.8 | <0.8 | <0.8 | <0.8 |
| Metronidazole | <0.8 | <0.8 | <0.8 | <0.8 | <0.8 | <0.8 | 12.5 | 12.4 | <0.8 | <0.8 |
| 23 | 1.5 | 1.5 | <0.8 | <0.8 | <0.8 | <0.8 | <0.8 | <0.8 | 1.5 | 3.1 |
| Metronidazole | <0.8 | 1.5 | <0.8 | <0.8 | <0.8 | <0.8 | 12.5 | 50 | 1.5 | 3.1 |
| 24 | <0.8 | <0.8 | <0.8 | <0.8 | <0.8 | <0.8 | <0.8 | <0.8 | <0.8 | <0.8 |
| Metronidazole | <0.8 | 1.5 | <0.8 | <0.8 | <0.8 | <0.8 | 12.5 | 50 | 1.5 | 3.1 |
| 25 | 1.5 | 3.1 | 1.5 | 1.5 | 1.5 | 1.5 | 1.5 | 1.5 | <0.8 | <0.8 |
| Metronidazole | <0.8 | <0.8 | <0.8 | <0.8 | 1.5 | 1.5 | 12.5 | 12.5 | 1.5 | 1.5 |
| 26 | <0.8 | <0.8 | 1.5 | 1.5 | <0.8 | <0.8 | <0.8 | <0.8 | <0.8 | <0.8 |
| Metronidazole | <0.8 | <0.8 | <0.8 | <0.8 | 1.5 | 1.5 | 12.5 | 12.5 | 1.5 | 1.5 |
| 27 | 1.5 | 1.5 | <0.8 | <0.8 | <0.8 | <0.8 | 1.5 | 1.5 | 1.5 | 3.1 |
| Metronidazole | <0.8 | 1.5 | <0.8 | <0.8 | <0.8 | <0.8 | 12.5 | 50 | 1.5 | 3.1 |
| 28 | <0.8 | <0.8 | <0.8 | <0.8 | <0.8 | <0.8 | <0.8 | <0.8 | <0.8 | 1.5 |
| Metronidazole | <0.8 | 1.5 | <0.8 | <0.8 | <0.8 | <0.8 | 12.5 | 50 | 1.5 | 3.1 |
| 29 | — | — | <0.8 | <0.8 | <0.8 | <0.8 | <0.8 | <0.8 | <0.8 | <0.8 |
| Metronidazole | — | — | <0.8 | <0.8 | <0.8 | <0.8 | 12.5 | 12.5 | <0.8 | <0.8 |
| 30 | <0.8 | <0.8 | <0.8 | 1.5 | <0.8 | <0.8 | <0.8 | <0.8 | <0.8 | <0.8 |
| Metronidazole | <0.8 | <0.8 | <0.8 | 3.1 | <0.8 | <0.8 | 12.5 | 12.5 | 1.5 | 3.1 |
| 31 | <0.8 | <0.8 | <0.8 | <0.8 | <0.8 | <0.8 | <0.8 | <0.8 | <0.8 | <0.8 |
| Metronidazole | <0.8 | <0.8 | <0.8 | 3.1 | <0.8 | <0.8 | 12.5 | 12.5 | 1.5 | 3.1 |
| 32 | <0.8 | <0.8 | 1.5 | 1.5 | <0.8 | <0.8 | <0.8 | <0.8 | <0.8 | <0.8 |
| Metronidazole | <0.8 | <0.8 | <0.8 | 3.1 | <0.8 | <0.8 | 12.5 | 12.5 | 1.5 | 3.1 |
| 33 | <0.8 | <0.8 | <0.8 | <0.8 | <0.8 | <0.8 | <0.8 | <0.8 | <0.8 | <0.8 |
| Metronidazole | <0.8 | <0.8 | <0.8 | <0.8 | <0.8 | <0.8 | 12.5 | 12.5 | <0.8 | <0.8 |
| 34 | <0.8 | <0.8 | <0.8 | <0.8 | <0.8 | <0.8 | <0.8 | <0.8 | <0.8 | <0.8 |
| Metronidazole | <0.8 | <0.8 | <0.8 | <0.8 | <0.8 | <0.8 | 12.5 | 12.5 | <0.8 | <0.8 |
| 35 | <0.8 | <0.8 | <0.8 | <0.8 | <0.8 | <0.8 | <0.8 | <0.8 | <0.8 | <0.8 |
| Metronidazole | <0.8 | <0.8 | <0.8 | 3.1 | <0.8 | <0.8 | 12.5 | 12.5 | 1.5 | 3.1 |

EXAMPLE 41

Utilizing the procedures described in Example 40, the anti-anaerobic activity of certain compounds of the present invention was demonstrated utilizing an additional 10 strains of various anaerobic bacteria.

The MIC values obtained are indicated in Table 2. A blank in the table represented by a "—" indicates that the assay was not conducted using the strain indicated.

TABLE 2
MIC vs Panel of Anaerobes

| Organism | (14) | (15) | (16) | (17) | (18) | (19) | (20) | (22) | MZ |
|---|---|---|---|---|---|---|---|---|---|
| Clostridium perfringens NCTC 523 | 25 | 1.5 | <0.8 | <0.8 | <0.8 | 1.5 | 1.5 | <0.8 | <0.8 |
| Clostridium perfringens NCTC 8237 | 25 | 12.5 | 12.5 | 6.2 | 6.2 | 1.5 | 1.5 | 6.2 | 1.5 |
| Costridium difficile NCIB 10666 | 1.5 | 1.5 | <0.8 | <0.8 | <0.8 | — | <0.8 | <0.8 | <0.8 |
| Campylobacter fetus ss. jejuni ATCC 29428 | 100 | — | — | 100 | — | — | 25 | 50 | >100 |
| Campylobacter fetus ss. jejuni NCTC 10842 | 50 | — | — | 50 | — | 6.2 | 6.2 | 50 | 3.1 |
| Fusobacterium necrophorum ATCC 11295 | 25 | <0.8 | <0.8 | 3.1 | <0.8 | <0.8 | 1.5 | <0.8 | 6.2 |
| Bacteroides melanogenicus NCTC 9336 | 100 | 100 | 25 | >100 | 25 | — | 50 | >100 | >100 |
| Peptococcous magnus | 100 | <0.8 | <0.8 | — | <0.8 | <0.8 | 25 | — | <0.8 |
| Peptostreptococcus | 100 | 100 | 25 | >100 | 25 | — | 50 | 100 | 100 |
| Propionebacterium acnes NCTC 737 | >100 | >100 | 100 | >100 | 100 | — | >100 | >100 | >100 |

| Organism | (23) | (24) | (25) | (26) | (29) | (30) | (31) | (32) | (39) | MZ |
|---|---|---|---|---|---|---|---|---|---|---|
| C. perfringens NCTC 523 | 1.5 | 1.5 | 3.1 | 1.5 | 1.5 | 6.2 | 3.1 | <0.8 | 1.5 | |
| C. perfringens NCTC 8237 | 6.2 | 6.2 | 3.1 | 1.5 | — | 12.5 | 12.5 | 6.2 | 6.2 | |
| C. difficile NCIB 10666 | 1.5 | <0.8 | 1.5 | <0.8 | <0.8 | <0.8 | <0.8 | — | 1.5 | |
| Camp. fetus ss. jejuni ATCC 29428 | 100 | 50 | 100 | 50 | 50 | 100 | 100 | — | 50 | |
| Camp. fetus | 100 | 100 | 6.2 | 25 | 100 | 100 | 50 | <0.8 | 25 | |

TABLE 2-continued

| MIC vs Panel of Anaerobes | | | | | | | | | |
|---|---|---|---|---|---|---|---|---|---|
| ss. jejuni NCTC 10842 | | | | | | | | | |
| F. necrophorum ATCC 11295 | <0.8 | <0.8 | 31 | 1.5 | 6.2 | 3.1 | 3.1 | <0.8 | 1.5 |
| B. melanogenicus ATCC 15032 | >100 | 100 | >100 | 100 | 100 | >100 | >100 | — | 100 |
| P. magnus | — | — | 100 | 12.5 | <0.8 | — | — | <0.8 | — |
| P. anaerobius | 100 | 100 | 100 | 50 | <0.8 | 100 | 100 | — | 100 |
| P. acnes NCTC 737 | >100 | 100 | >100 | 100 | >100 | >100 | >100 | — | 100 |

EXAMPLE 42

Determination of in vivo anti-anaerobe activity—mouse hepatic necrosis 500 ml volumes of basic anaerobe broth (nutrient broth No. 2) (LABM) 28 g/L, haemin 5 mg/L, vitamin K 0.5 mg/L, and cysteine hydrochloride 0.5 g/L) were inoculated from a cooked meat broth stock culture of *B. fragilis* 23745 which had been inoculated from the original cooked meat broth stock so that subculturing was kept to a minimum. Cultures were incubated anaerobically in an anaerobic chamber. When the broths reached a heavy turbidity (24–48 hours), they were aliquoted into small bottles to which inactivated horse serum was added to 10%, together with a few drops of neutralized ascorbate (100 mg/ml), before snap freezing and storing at $-20°$ C. The viable count was $10^{10}$ organisms/ml.

Rat faeces or mouse bowel contents were mixed with a small volume of water and autoclaved, then homogenized. After standing overnight, they were autoclaved again and then freeze-dried in small batches.

Stock inoculum was thawed and diluted to yield a viable count of $5\times10^8$ organisms/ml with fresh broth, and sterile faecal material was added to a final concentration of 2% w/v. Animals (groups of ten male BALB/c mice weighing 18–22 g) were inoculated intraperitoneally with 0.2 ml of the inoculum so that each receives $10^8$ *B. fragilis*.

Test compounds were dissolved in polyethylene glycol 200 or dimethylsulfoxide and then diluted with water or saline to give the appropriate final concentration. The stock solution was used to prepare a two-fold dilution series having a final dose range of 2.5–40 mg/kg. The initial dose was given p.o. immediately after infection and twice daily thereafter for 2 days. Animals were sacrificed on the third day using carbon dioxide or cervical dislocation. Control animals received dosing vehicle only. Metronidazole was used as a positive control.

At the end of the experimental period the animals' livers were removed aseptically with care not to puncture the bowel and transferred to Universal bottles of peptone water and kept on ice.

The livers were homogenized at low speed with care to prevent frothing and the bottles were gassed out again. Homogenate was diluted by transferring 0.1 ml of the homogenate to a 10 ml aliquot of peptone water diluent, and the diluted homogenate was spread on basic anaerobic agar at 0.1 ml per petri-dish. The media used for this purpose must have either been prepared freshly, or stored in plastic bags in which the air has been replaced by anaerobic gas mixture, or stored in anaerobic jars. After the homogenate was spread on the petri-dish, the petri-dishes were left exposed to air for the minimum possible time (and never more than 15 minutes) so that small numbers of Bacteroides were recovered and grown from the inoculum.

Cultures were incubated anaerobically for 48 hours in a Forma Anaerobic Chamber at 37° C. At the end of this period, the resultant colonies were counted using an AMS 40-10 Image Analyser. The mean number of viable organisms were calculated for each treatment group and the data analyzed using analysis of variance and two sample t-test for comparison of individual groups. Results were expressed as the reduction in log colony forming units/ml of liver homogenate for each treatment group compared to the untreated controls. From the dose response curves, the dose giving 1 log (90%) reduction is calculated for each compound and the efficacy of the test compound relative to metronidazole is determined.

Under these test conditions, metronidazole gives a reduction in *B. fragilis*, of 3–3.5 $\log_{10}$ at 40 mg/kg (p.o.).

The activities of the compounds described above are given in Table 3.

TABLE 3

| DOSE GIVING 1 LOG REDUCTION | | |
|---|---|---|
| Compound of Example No. | mg/kg (µM/Kg) | Metronidazole |
| (15) | 4.1 (13.4) | 2.4 (14.2) |
| (16) | 0.8 (2.6) | 2.4 (9.3) |
| (17) | 3.2 (9.3) | 3.6 (10.8) |
| (18) | 17.4 (53.4) | 3.6 (20.8) |
| (19) | 1.5 (4.6) | 1.9 (11.0) |
| (20) | 4.2 (13.0) | 2.2 (12.7) |
| (21) | 2.5 (6.8) | 1.6 (9.3) |
| (22) | 2.7 (7.3) | 1.9 (11.2) |
| (23) | 1.9 (6.0) | 2.1 (12.1) |
| (24) | 2.2 (6.8) | 2.1 (12.1) |
| (25) | 1.9 (5.75) | 1.85 (10.8) |
| (26) | 3.4 (10.1) | 1.85 (10.8) |
| (27) | 2.5 (7.4) | 2.1 (12.1) |
| (28) | 2.5 (7.4) | 1.9 (11.0) |
| (29) | 3.5 (10.1) | 1.9 (11.0) |
| (31) | 1.0 (3.0) | 1.5 (8.6) |
| (32) | 0.95 (3.3) | 1.5 (8.6) |
| (33) | 0.9 (2.85) | 2.05 (12.0) |
| (34) | 2.7 (9.3) | 2.05 (12.0) |
| (39) | 0.7 (1.8) | 1.0 (5.9) |

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula

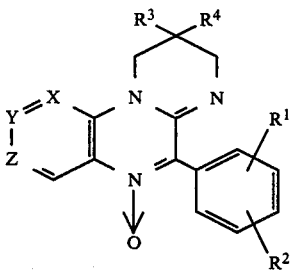

wherein
R¹ and R² are independently selected from the class consisting of hydrogen, halo, $C_1$–$C_6$ alkyl, and $C_1$–$C_6$ alkoxy;
R³ and R⁴ are independently hydrogen or $C_1$–$C_6$ alkyl or R³ and R⁴ together may be a

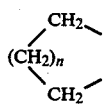

group wherein n is an integer of from 0 to 4; and
X, Y and Z are independently —CH— or —N═ provided that one and only one of X, Y or Z must be —N═;
and pharmaceutically acceptable salts thereof.

2. A compound according to claim 1 of the formula

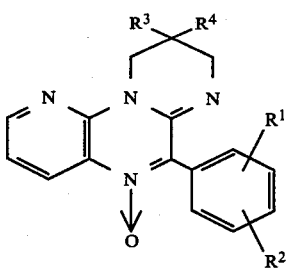

wherein
R¹ and R² are independently selected from the class consisting of hydrogen, halo, $C_1$–$C_6$ alkyl, and $C_1$–$C_6$ alkoxy;
R³ and R⁴ are independently hydrogen or $C_1$–$C_6$ alkyl or R³ and R⁴ together may be a

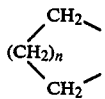

group wherein n is an integer of from 0 to 4;
and pharmaceutically acceptable salts thereof.

3. A compound according to claim 2 wherein R³ and R⁴ are independently $C_1$–$C_6$ alkyl.

4. A compound according to claim 3 wherein R¹ and R² are hydrogen.

5. A compound according to claim 4 which is 2,3-dihydro-2,2-dimethyl-5-phenyl-1H-pyrimido[1,2-a]pyrido[3,2-e]pyrazine 6-oxide.

6. A compound according to claim 4 which is 2,3-dihydro-2-ethyl-2-methyl-5-phenyl-1H-pyrimido[1,2-a]pyrido[3,2-e]pyrazine 6-oxide.

7. A compound according to claim 4 which is 2,3-dihydro-2-methyl-5-phenyl-2-propyl-1H-pyrimido[1,2-a]pyrido[3,2-e]pyrazine 6-oxide.

8. A compound according to claim 4 which is 2,3-dihydro-2,2-diethyl-5-phenyl-1H-pyrimido[1,2-a]pyrido[3,2-e]pyrazine 6-oxide.

9. A compound according to claim 4 which is 2,3-dihydro-2,2-dipropyl-5-phenyl-1H-pyrimido[1,2-a]pyrido[3,2-e]pyrazine 6-oxide.

10. A compound according to claim 3 wherein R¹ is $C_1$–$C_6$ alkyl and R² is hydrogen.

11. A compound according to claim 10 which is 2,3-dihydro-2,2-dimethyl-5-(4-methylphenyl)-1H-pyrimido[1,2-a]pyrido[3,2-e]pyrazine 6-oxide.

12. A compound according to claim 10 which is 2,3-dihydro-2-ethyl-2-methyl-5-(4-methylphenyl)-1H-pyrimido[1,2-a]pyrido[3,2-e]pyrazine 6-oxide.

13. A compound according to claim 3 wherein R¹ is halo and R² is hydrogen.

14. A compound according to claim 13 which is 2,3-dihydro-5-(4-chlorophenyl)-2,2-dimethyl-1H-pyrimido[1,2-a]pyrido[3,2-e]pyrazine 6-oxide.

15. A compound according to claim 13 which is 2,3-dihydro-2,2-dimethyl-5-(4-fluorophenyl)-1H-pyrimido[1,2-a]pyrido[3,2-e]pyrazine 6-oxide.

16. A compound according to claim 3 wherein R¹ and R² are independently $C_1$–$C_6$ alkoxy.

17. A compound according to claim 16 which is 2,3-dihydro-5-(3,4-dimethoxyphenyl)-2,2-dimethyl-1H-pyrimido[1,2-a]pyrido[3,2-e]pyrazine 6-oxide.

18. A compound according to claim 2 wherein R³ is $C_1$–$C_6$ alkyl and R⁴ is hydrogen.

19. A compound according to claim 18 wherein R¹ and R² are hydrogen.

20. A compound according to claim 19 which is 2,3-dihydro-2-methyl-5-phenyl-1H-pyrimido[1,2-a]pyrido[3,2-e]pyrazine 6-oxide.

21. A compound according to claim 2 wherein R³ and R⁴ together are a

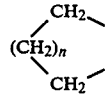

group wherein n is an integer of from 0 to 4.

22. A compound according to claim 21 wherein n is 3 and R¹ and R² are hydrogen.

23. A compound according to claim 22 which is spiro[cyclohexane-1,2'-[2,3]-dihydro-[5]-phenyl-[1H]pyrimido[1,2-a]pyrido[3,2-e]pyrazine[6]-oxide].

24. A compound according to claim 1 of the formula

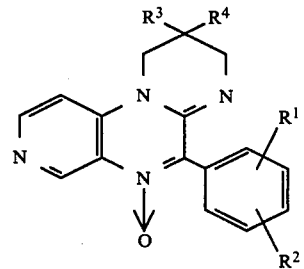

wherein

R¹ and R² are independently selected from the class consisting of hydrogen, halo, $C_1$–$C_6$ alkyl, and $C_1$–$C_6$ alkoxy;

R³ and R⁴ are independently hydrogen or $C_1$–$C_6$ alkyl or R³ and R⁴ together may be a

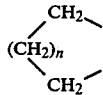

group wherein n is an integer of from 0 to 4; and pharmaceutically acceptable salts thereof.

25. A compound according to claim 24 wherein R³ and R⁴ are independently $C_1$–$C_6$ alkyl.

26. A compound according to claim 25 wherein R¹ and R² are hydrogen.

27. A compound according to claim 26 which is 2,3-dihydro-2,2-dimethyl-5-phenyl-1H-pyrimido[1,2-a]pyrido[3,4-e]pyrazine 6-oxide.

28. A compound according to claim 26 which is 2,3-dihydro-2-ethyl-2-methyl-5-phenyl-1H-pyrimido[1,2-a]pyrido[3,4-e]pyrazine 6-oxide.

29. A compound according to claim 26 which is 2,3-dihydro-2-methyl-5-phenyl-2-propyl-1H-pyrimido[1,2-a]pyrido[3,4-e]pyrazine 6-oxide.

30. A compound according to claim 26 which is 2,3-diphenyl-2,2-diethyl-5-phenyl-1H-pyrimido[1,2-a]pyrido[3,4-e]pyrazine 6-oxide.

31. A compound according to claim 26 which is 2,3-dihydro-2,2-dipropyl-5-phenyl-1H-pyrimido[1,2-a]pyrido[3,4-e]pyrazine 6-oxide.

32. A compound according to claim 25 wherein R¹ is $C_1$–$C_6$ alkyl and R² is hydrogen.

33. A compound according to claim 32 which is 2,3-dihydro-2,2-dimethyl-5-(4-methylphenyl)-1H-pyrimido[1,2-a]pyrido[3,4-e]pyrazine 6-oxide.

34. A compound according to claim 32 which is 2,3-dihydro-2-ethyl-2-methyl-5-(4-methylphenyl)-1H-pyrimido[1,2-a]pyrido[3,4-e]pyrazine 6-oxide.

35. A compound according to claim 25 wherein R¹ is halo and R² is hydrogen.

36. A compound according to claim 35 which is 2,3-dihydro-5-(4-chlorophenyl)-2,2-dimethyl-1H-pyrimido[1,2-a]pyrido[3,4-e]pyrazine 6-oxide.

37. A compound according to claim 35 which is 2,3-dihydro-2,2-dimethyl-5-(4-fluorophenyl)-1H-pyrimido[1,2-a]pyrido[3,4-e]pyrazine 6-oxide.

38. A compound according to claim 25 wherein R¹ and R² are independently $C_1$–$C_6$ alkoxy.

39. A compound according to claim 38 which is 2,3-dihydro-5-(3,4-dimethoxyphenyl)-2,2-dimethyl-1H-pyrimido[1,2-a]pyrido[3,4-e]pyrazine 6-oxide.

40. A compound according to claim 24 wherein R³ is $C_1$–$C_6$ alkyl and R⁴ is hydrogen.

41. A compound according to claim 40 wherein R¹ and R² are hydrogen.

42. A compound according to claim 41 which is 2,3-dihydro-2-methyl-5-phenyl-1H-pyrimido[1,2-a]pyrido[3,4-e]pyrazine 6-oxide.

43. A compound according to claim 24 wherein R³ and R⁴ together are a

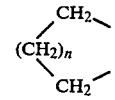

group wherein n is an integer of from 0 to 4.

44. A compound according to claim 43 wherein n is 3 and R¹ and R² are hydrogen.

45. A compound according to claim 44 which is spiro[cyclohexane-1,2'-[2,3]-dihydro-[5]-phenyl-[1H]pyrimido[1,2-a]pyrido[3,4-e]pyrazine [6]-oxide].

46. A compound according to claim 1 of the formula

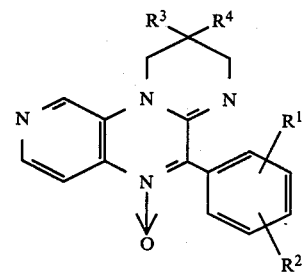

wherein

R¹ and R² are independently selected from the class consisting of hydrogen, halo, $C_1$–$C_6$ alkyl, and $C_1$–$C_6$ alkoxy;

R³ and R⁴ are independently hydrogen or $C_1$–$C_6$ alkyl or R³ and R⁴ together may be a

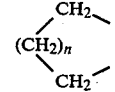

group wherein n is an integer of from 0 to 4; and pharmaceutically acceptable salts thereof.

47. A compound according to claim 46 wherein R³ and R⁴ are independently $C_1$–$C_6$ alkyl.

48. A compound according to claim 47 wherein R¹ and R² are hydrogen.

49. A compound according to claim 48 which is 2,3-dihydro-2,2-dimethyl-5-phenyl-1H-pyrimido[1,2-a]pyrido[4,3-e]pyrazine 6-oxide.

50. A pharmaceutical composition comprising a compound according to claim 1 together with a pharmaceutically acceptable carrier.

51. A pharmaceutical composition according to claim 50 wherein said compound is selected from the group consisting of:

2,3-dihydro-2,2-dimethyl-5-phenyl-1H-pyrimido[1,2-a]pyrido[3,2-e]pyrazine 6-oxide, 2,3-dihydro-2-ethyl-2-methyl-5-phenyl-1H-pyrimido[1,2-a]pyrido[3,2-e]pyrazine 6-oxide, 2,3-dihydro-2-methyl-5-phenyl-2-propyl-1H-pyrimido[1,2-a]pyrido[3,2-e]pyrazine 6-oxide, 2,3-dihydro-2,2-diethyl-5-phenyl-1H-pyrimido[1,2-a]pyrido[3,2-e]pyrazine 6-oxide, 2,3-dihydro-2,2-dipropyl-5-phenyl-1H-pyrimido[1,2-a]pyrido[3,2-e]pyrazine 6-oxide, 2,3-dihydro-2,2-dimethyl-5-(4-methylphenyl)-1H-pyrimido[1,2-a]pyrido[3,2-e]pyrazine 6-oxide, 2,3-dihydro-2-ethyl-2-methyl-5-(4-methylphenyl)-1H-pyrimido[1,2-a]pyrido[3,2-e]pyrazine 6-oxide,
2,3-dihydro-5-(4-chlorophenyl)-2,2-dimethyl-1H-pyrimido[1,2-a]pyrido[3,2-e]pyrazine 6-oxide,
2,3-dihydro-2,2-dimethyl-5-(4-fluorophenyl)-1H-pyrimido[1,2-a]pyrido[3,2-e]pyrazine 6-oxide,
2,3-dihydro-5-(3,4-dimethoxyphenyl)-2,2-dimethyl-1H-pyrimido[1,2-a]pyrido[3,2-e]pyrazine 6-oxide,
2,3-dihydro-2-methyl-5-phenyl-1H-pyrimido[1,2-a]pyrido[3,2-e]pyrazine 6-oxide,
spiro[cyclohexane-1,2'-[2,3]-dihydro-[5]-phenyl-[1H]-pyrimido[1,2-a]pyrido[3,2-e]pyrazine[6]-oxide],
2,3-dihydro-2,2-dimethyl-5-phenyl-1H-pyrimido[1,2-a]pyrido[3,4-e]pyrazine 6-oxide,
2,3-dihydro-2-ethyl-2-methyl-5-phenyl-1H-pyrimido[1-,2a]pyrido[3,4-e]pyrazine 6-oxide,
2,3-dihydro-2-methyl-5-phenyl-2-propyl-1H-pyrimido[1,2-a]pyrido[3,4-e]pyrazine 6-oxide,
2,3-dihydro-2,2-diethyl-5-phenyl-1H-pyrimido[1,2-a]pyrido[3,4-e]pyrazine 6-oxide,
2,3-dihydro-2,2-dipropyl-5-phenyl-1H-pyrimido[1,2-a]pyrido[3,4-e]pyrazine 6-oxide,
2,3-dihydro-2,2-dimethyl-5-(4-methylphenyl)-1H-pyrimdo[1,2-a]pyrido[3,4-e]pyrazine 6-oxide,
2,3-dihydro-2-ethyl-2-methyl-5-(4-methylphenyl)-1H-pyrimido[1,2-a]pyrido[3,4-e]pyrazine 6-oxide,
2,3-dihydro-5-(4-chlorophenyl)-2,2-dimethyl-1H-pyrimido[1,2-a]pyrido[3,4-e]pyrazine 6-oxide,
2,3-dihydro-2,2-dimethyl-5-(4-fluorophenyl)-1H-pyrimido[1,2-a]pyrido[3,4-e]pyrazine 6-oxide,
2,3-dihydro-5-(3,4-dimethoxyphenyl)-2,2-dimethyl-1H-pyrimido[1,2-a]pyrido[3,4-e]pyrazine 6-oxide,
2,3-dihydro-2-methyl-5-phenyl-1H-pyrimido[1,2-a]pyrido[3,4-e]pyrazine 6-oxide,
spiro[cyclohexane-1,2'-[2,3]-dihydro-[5]-phenyl-[1H]pyrimido[1,2-a]pyrido[3,4-e]pyrazine[6]-oxide], and
2,3-dihydro-2,2-dimethyl-5-phenyl-1H-pyrimido[1,2-a]pyrido[3,4-e]pyrazine 6-oxide.

52. A method for treating anaerobic infections in mammals comprising administering a therapeutically effective dose of at least one compound of claim 1 to a mammal in need of such treatment.

53. A method according to claim 52 wherein said compound is selected from the group consisting of:
2,3-dihydro-2,2-dimethyl-5-phenyl-1H-pyrimido[1,2-a]pyrido[3,2-e]pyrazine 6-oxide,
2,3-dihydro-2-ethyl-2-methyl-5-phenyl-1H-pyrimido[1,2-a]pyrido[3,2-e]pyrazine 6-oxide,
2,3-dihydro-2-methyl-5-phenyl-2-propyl-1H-pyrimido[1,2-a]pyrido[3,2-e]pyrazine 6-oxide,
2,3-dihydro-2,2-diethyl-5-phenyl-1H-pyrimido[1,2-a]pyrido[3,2-e]pyrazine 6-oxide,
2,3-dihydro-2,2-dipropyl-5-phenyl-1H-pyrimido[1,2-a]pyrido[3,2-e]pyrazine 6-oxide,
2,3-dihydro-2,2-dimethyl-5-(4-methylphenyl)-1H-pyrimido[1,2-a]pyrido[3,2-e]pyrazine 6-oxide,
2,3-dihydro-2-ethyl-2-methyl-5-(4-methylphenyl)-1H-pyrimido[1,2-a]pyrido[3,2-e]pyrazine 6-oxide,
2,3-dihydro-5-(4-chlorophenyl)-2,2-dimethyl-1H-pyrimido[1,2-a]pyrido[3,2-e]pyrazine 6-oxide,
2,3-dihydro-2,2-dimethyl-5-(4-fluorophenyl)-1H-pyrimido[1,2-a]pyrido[3,2-e]pyrazine 6-oxide,
2,3-dihydro-5-(3,4-dimethoxyphenyl)-2,2-dimethyl-1H-pyrimido[1,2a]pyrido[3,2-e]pyrazine 6-oxide,
2,3-dihydro-2-methyl-5-phenyl-1H-pyrimido[1,2-a]pyrido[3,2-e]pyrazine 6-oxide,
spiro[cyclohexane-1,2'-[2,3]-dihydro-[5]-phenyl-[1H]-pyrimido[1,2-a]pyrido[3,2-e]pyrazine [6]-oxide],
2,3-dihydro-2,2-dimethyl-5-phenyl-1H-pyrimido[1,2-a]pyrido[3,4-e]pyrazine 6-oxide,
2,3-dihydro-2-ethyl-2-methyl-5-phenyl-1H-pyrimido[1,2-a]pyrido[3,4-e]pyrazine 6-oxide,
2,3-dihydro-2-methyl-5-phenyl-2-propyl-1H-pyrimido[1,2-a]pyrido[3,4-e]pyrazine 6-oxide,
2,3-dihydro-2,2-diethyl-5-phenyl-1H-pyrimido[1,2-a]pyrido[3,4-e]pyrazine 6-oxide,
2,3-dihydro-2,2-dipropyl-5-phenyl-1H-pyrimido[1,2-a]pyrido[3,4-e]pyrazine 6-oxide,
2,3-dihydro-2,2-dimethyl-5-(4-methylphenyl)-1H-pyrimido[1,2-a]pyrido[3,4-e]pyrazine 6-oxide,
2,3-dihydro-2-ethyl-2-methyl-5-(4-methylphenyl)-1H-pyrimido[1,2-a]pyrido[3,4-e]pyrazine 6-oxide,
2,3-dihydro-5-(4-chlorophenyl)-2,2-dimethyl-1H-pyrimido[1,2-a]pyrido[3,4-e]pyrazine 6-oxide,
2,3-dihydro-2,2-dimethyl-5-(4-fluorophenyl)-1H-pyrimido[1,2-a]pyrido[3,4-e]pyrazine 6-oxide,
2,3-dihydro-5-(3,4-dimethoxyphenyl)-2,2-dimethyl-1H-pyrimido[1,2-a]pyrido[3,4-e]pyrazine 6-oxide,
2,3-dihydro-2-methyl-5-phenyl-1H-pyrimido[1,2-a]pyrido[3,4-e]pyrazine 6-oxide,
spiro[cyclohexane-1,2'-[2,3]-dihydro-[5]-phenyl-[1H]pyrimido[1,2-a]pyrido[3,4-e]pyrazine[6]-oxide], and
2,3-dihydro-2,2-dimethyl-5-phenyl-1H-pyrimido[1,2-a]pyrido[4,3-e]pyrazine 6-oxide.

* * * * *

UNITED STATES PATENT AND TRADEMARK OFFICE
CERTIFICATE OF CORRECTION

PATENT NO. : 4,761,414

DATED : August 2, 1988

INVENTOR(S) : Ellames, et al.

It is certified that error appears in the above-identified patent and that said Letters Patent is hereby corrected as shown below:

Column 18, line 38, reading " a "13" indicates" should read -- a "__" indicates --.

Column 25, Claim 30, line 30, reading "diphenyl" should read -- dihydro --.

Column 26, line 60, reading "pyrazine6-oxide" should read -- pyrazine 6-oxide --.

Column 27, lines 16-17, reading "[1-,2a]" should read -- [1,2-a] --.

Signed and Sealed this

Eleventh Day of September, 1990

Attest:

HARRY F. MANBECK, JR.

*Attesting Officer*    *Commissioner of Patents and Trademarks*